US012806618B2

(12) United States Patent
Laugharn, Jr. et al.

(10) Patent No.: US 12,806,618 B2
(45) **Date of Patent: *Nov. 24, 2026**

(54) SAMPLE HOLDER WITH CONDUIT FOR RECEIVING A SAMPLE

(71) Applicant: Covaris, LLC, Woburn, MA (US)

(72) Inventors: James A. Laugharn, Jr., Boston, MA (US); Edward Ognibene, Belmont, MA (US); Andrew Briggs, Medford, MA (US); Paul Prokop, Woburn, MA (US); Todd Anthony Basque, West Newbury, MA (US); Jeremy Terry, Wilmington, MA (US)

(73) Assignee: Covaris, LLC, Woburn, MA (US)

( * ) Notice: Subject to any disclaimer, the term of this patent is extended or adjusted under 35 U.S.C. 154(b) by 540 days.

This patent is subject to a terminal disclaimer.

(21) Appl. No.: 18/363,973

(22) Filed: Aug. 2, 2023

(65) Prior Publication Data

US 2024/0042434 A1 Feb. 8, 2024

Related U.S. Application Data

(60) Provisional application No. 63/452,269, filed on Mar. 15, 2023, provisional application No. 63/395,590, filed on Aug. 5, 2022.

(51) Int. Cl.
*B01L 3/00* (2006.01)
*A61B 5/15* (2006.01)

(52) U.S. Cl.
CPC .. *B01L 3/502715* (2013.01); *A61B 5/150022* (2013.01); *A61B 5/150213* (2013.01);
(Continued)

(58) Field of Classification Search
CPC .. B01L 3/502715; B01L 3/5635; B01L 3/502; B01L 3/50825; B01L 2200/0684;
(Continued)

(56) References Cited

U.S. PATENT DOCUMENTS 3,630,191 A 12/1971 Gilford
3,779,083 A 12/1973 Ayres et al.
(Continued)

FOREIGN PATENT DOCUMENTS

WO WO 2017/210218 A1 12/2017
WO WO 2021/188594 A1 9/2021
WO WO 2021/208262 A1 10/2021

OTHER PUBLICATIONS

International Search Report and Written Opinion for International Application No. PCT/US2023/029386, mailed Jan. 30, 2024.
(Continued)

*Primary Examiner* — Benjamin R Whatley
(74) *Attorney, Agent, or Firm* — Wolf, Greenfield & Sacks, P.C.

(57) ABSTRACT

A sample holder for collecting a liquid sample, such as blood. The holder can include a vessel, a conduit having a proximal end extending from the vessel and a distal end positioned in the vessel, and a cap configured to engage with the vessel and create pressure to move a liquid sample in the conduit to move from the proximal end to the distal end. The vessel can include a fluid pathway to vent fluid from the vessel as the liquid sample is moved from the conduit into the vessel, and the cap can seal the fluid pathway closed. A desiccant can be used to support the conduit in the vessel and dry a blood sample during storage.

20 Claims, 15 Drawing Sheets

(52) U.S. Cl.
CPC .. *A61B 5/150343* (2013.01); *A61B 5/150351* (2013.01); *B01L 3/5635* (2013.01); *B01L 3/502* (2013.01); *B01L 3/50825* (2013.01); *B01L 2200/0684* (2013.01); *B01L 2300/042* (2013.01); *B01L 2300/044* (2013.01); *B01L 2300/046* (2013.01); *B01L 2300/0672* (2013.01); *B01L 2300/0832* (2013.01); *B01L 2300/0838* (2013.01); *B01L 2300/105* (2013.01)

(58) Field of Classification Search
CPC ......... B01L 2300/042; B01L 2300/044; B01L 2300/046; B01L 2300/0672; B01L 2300/0832; B01L 2300/0838; B01L 2300/105; A61B 5/150022; A61B 5/150213; A61B 5/150343; A61B 5/150351
See application file for complete search history.

(56) References Cited

U.S. PATENT DOCUMENTS

| | | | | |
|---|---|---|---|---|
| 3,983,037 | A | 9/1976 | Lee et al. | |
| 4,003,262 | A | 1/1977 | Gerarde et al. | |
| 4,469,110 | A | 9/1984 | Slama | |
| 4,589,421 | A | 5/1986 | Ullman | |
| 5,376,337 | A | 12/1994 | Seymour | |
| 5,409,667 | A | 4/1995 | Elson | |
| 5,494,646 | A | 2/1996 | Seymour | |
| 5,833,630 | A | 11/1998 | Kloth | |
| 6,319,209 | B1 | 11/2001 | Kriz | |
| 6,803,021 | B1 | 10/2004 | Bertling | |
| 9,295,416 | B2 | 3/2016 | Bartfield et al. | |
| 9,694,358 | B2 | 7/2017 | Luotola | |
| 10,180,421 | B2 | 1/2019 | Johnson et al. | |
| 10,499,840 | B2 | 12/2019 | Bartfield et al. | |
| 11,291,989 | B2 | 4/2022 | Morrison | |
| 11,304,638 | B2 | 4/2022 | Morrison | |
| 2001/0039058 | A1 | 11/2001 | Iheme et al. | |
| 2003/0207463 | A1 | 11/2003 | Iheme et al. | |
| 2011/0020195 | A1 | 1/2011 | Luotola | |
| 2014/0050620 | A1 | 2/2014 | Johnson et al. | |
| 2014/0105796 | A1 | 4/2014 | Nagy | |
| 2015/0212081 | A1 | 7/2015 | Catteruccia et al. | |
| 2016/0100783 | A1 | 4/2016 | Ivosevic et al. | |
| 2016/0121322 | A1 | 5/2016 | Fuller et al. | |
| 2016/0250630 | A1 * | 9/2016 | Foucault | G01N 33/491<br>436/177 |
| 2017/0042460 | A1 | 2/2017 | Holmes et al. | |
| 2017/0102299 | A1 | 4/2017 | Laugharn, Jr. et al. | |
| 2019/0168210 | A1 | 6/2019 | Anderson | |
| 2019/0299215 | A1 | 10/2019 | Guttman et al. | |
| 2020/0029878 | A1 | 1/2020 | Steiner et al. | |
| 2020/0170557 | A1 | 6/2020 | Ringold et al. | |
| 2020/0337620 | A1 | 10/2020 | Morrison et al. | |
| 2021/0283597 | A1 | 9/2021 | Kluge et al. | |
| 2021/0401411 | A1 | 12/2021 | Ringold et al. | |
| 2022/0024052 | A1 | 1/2022 | Wolton | |
| 2022/0061822 | A1 | 3/2022 | Robbins et al. | |
| 2023/0074519 | A1 * | 3/2023 | McDade | G01N 1/31 |
| 2024/0366129 | A1 | 11/2024 | Cruz et al. | |

OTHER PUBLICATIONS

Invitation to Pay Additional Fees for International Application No. PCT/US2023/029386, mailed Oct. 23, 2023.
International Preliminary Report on Patentability, mailed Feb. 20, 2025, for Application No. PCT/US2023/029386.

* cited by examiner

SAMPLE HOLDER WITH CONDUIT FOR RECEIVING A SAMPLE

RELATED APPLICATIONS

This Application is a non-provisional application claiming priority under 35 U.S.C. § 119 (e) to U.S. Provisional Application Ser. No. 63/452,269, filed Mar. 15, 2023 and U.S. Provisional Application Ser. No. 63/395,590 filed Aug. 5, 2022. The entire contents of these applications are incorporated herein by reference in their entirety.

BACKGROUND

1. Field of Invention

Methods and apparatus for sample holders.

2. Related Art

Sample holders, including individual tubes or vessels, are widely used in laboratory and other applications for collecting, holding and/or processing liquid samples, e.g., whole blood samples for diagnostic testing and research. Such vessels are used to expose a sample to a variety of different treatments, including exposure to sonic energy, heat/cooling cycles such as that used in PCR processing, and others.

SUMMARY

In some embodiments, a sample holder includes a vessel having a wall with an outer surface and defining an internal space. The vessel can be configured to receive and hold any suitable type of sample, such as a blood or other liquid sample. In some cases, the vessel can have an immobilizer such as a chemical material and/or physical structure suitable to interact with a blood or other liquid sample, e.g., to help keep the sample in a desired area of the vessel and/or treat the sample for storage or other processing. In some embodiments, the vessel can include a fluid pathway from the internal space to an external environment, e.g., the vessel can include an opening or other vent that extends through a wall of the vessel. A conduit, such as a capillary tube, can be configured to receive a sample and can have a distal end positioned in the internal space of the vessel and a proximal end extending from the internal space. In some cases, the conduit can be configured to draw a blood sample into the proximal end of the conduit, e.g., by contacting the proximal end of the tube to a pool of blood which is drawn into the conduit by capillary action. In some embodiments, a conduit holder can be arranged to support the conduit in the internal space of the vessel. For example, a part of the vessel can be configured to engage with the conduit to hold the conduit in place in the vessel, e.g., so that the distal end of the conduit is held above a bottom of the vessel. In some cases, the conduit holder can include a desiccant configured to receive moisture from a blood or other sample in the internal space so as to dry the blood sample, e.g., in a way suitable for extended storage. In cases where the vessel includes a fluid pathway (e.g., an opening in a wall of the vessel), the internal space of the vessel can be sealed closed except for the fluid pathway and the conduit. That is, the vessel can be configured so that fluid can enter the internal space of the vessel only by way of the fluid pathway or the conduit. A cap can be configured to receive the proximal end of the conduit and engage with the vessel such that movement of the cap relative to the vessel from a first position toward a second position relative to the vessel causes fluid pressure suitable to move a blood sample from the conduit into the internal space. That is, the cap and vessel can act as a kind of pump to force blood or other liquid material in the conduit to flow from the proximal end to the distal end and into the internal space of the vessel (e.g., at the vessel bottom). In some cases, movement of the cap from the first position to the second position can cause fluid to move from the internal space through the fluid pathway, e.g., to exit the vessel. For example, as blood or other liquid in the conduit moves into the vessel, gas may be vented from the internal space via the fluid pathway. This can help avoid pressurizing the internal space of the vessel, which can prevent or otherwise resist the cap from being moved relative to the vessel. In some cases, the cap closes the fluid pathway when in the second position, e.g., the cap can cover an opening in the vessel wall to seal the fluid pathway closed. This can allow the cap to seal the internal space closed, preventing gas and/or liquid from exiting and/or entering the internal space. In some embodiments, the vessel can include a lower portion having a cavity that receives the distal end of the conduit and an upper portion positioned around the conduit and configured to engage with the cap. For example, the upper portion can have a larger diameter or size than the lower portion, which can allow the upper portion to provide an increased volume of gas flow through the conduit as the cap is moved relative to the vessel. The smaller diameter or size of the lower portion of the vessel can reduce a volume of the internal space of the vessel and thereby improve drying of a blood or other sample.

In some embodiments, the cap includes a cavity configured to receive a portion of the vessel to engage the cap with the vessel. Thus, the cap and the vessel can be configured to create a pressure above ambient pressure in response to movement of the portion of the vessel into the cavity. In some cases, the cavity can be configured to receive the proximal end of the conduit when the cap is engaged with the vessel, and the pressure above ambient pressure can be suitable to force a blood sample in the conduit to move through the distal end and into the internal space of the vessel (e.g., at the bottom of the vessel). In some embodiments, with the cap disengaged from the vessel, the internal space of the vessel is sealed closed except for a path through the conduit from the proximal to the distal end and the fluid pathway (e.g., which may be defined in part by an opening through the wall of the vessel). With the cap engaged with the vessel and in the first position, the internal space can be sealed closed except for the fluid pathway (i.e., the path through the conduit can be closed by the cap), and with the cap engaged with the vessel and in the second position, the internal space can be sealed completely closed (i.e., the path through the conduit and the fluid pathway of the vessel can be sealed closed).

In some cases, a desiccant can be in the internal space and configured to dry a blood sample enclosed in the internal space. For example, a conduit holder that supports the conduit in the vessel can include a desiccant. The desiccant can engage with an inner surface of the wall of the vessel and support the conduit in the vessel at least in part, e.g., a portion of the vessel may contact and aid in supporting the conduit as well. In some embodiments, the desiccant has a tubular shape and a portion of the conduit passes through the desiccant. For example, the desiccant can include first and second clamshell portions that sandwich the conduit. Each clamshell portion can include a groove to receive the conduit, and can include one or more standoffs to define a channel along a length of the desiccant. The channel can provide a fluid pathway in the vessel and/or allow a user to visualize a portion of the conduit and/or provide an increased surface area of the desiccant that is exposed to a blood or other liquid sample in the vessel.

In some cases, a method of collecting a blood sample includes providing a conduit at least partially within an internal space of a vessel. A proximal end of the conduit can be contacted to blood to draw the blood into the conduit, e.g., the conduit can include a capillary tube configured to draw blood into the tube by capillary action, or the blood can be moved into the conduit by negative or positive pressure in the conduit. A cap can be moved from a first position toward a second position relative to the vessel to create a positive pressure at the proximal end of the conduit and force the blood to move out of the conduit and into the internal space of the vessel. Fluid such as gas can be vented from the internal space of the vessel as blood moves from the conduit and into the internal space of the vessel, and the cap can be positioned at the second position relative to the vessel to seal the internal space closed.

In some cases, venting fluid from the vessel includes venting fluid from the internal space via a fluid pathway defined in part by an opening through a wall of the vessel. Positioning the cap at the second position can include positioning the cap to cover the opening, e.g., to seal the internal space of the vessel closed.

In some embodiments, moving the cap includes receiving a portion of the vessel into a cavity of the cap to engage the cap with the vessel and create the positive pressure and thus flow of blood from the distal end of the conduit. For example, moving the cap can include moving a volume of gas through the conduit from the proximal end to the distal end that is greater than a volume of the conduit.

In some embodiments, the method can include drying the blood in the sealed internal space by a desiccant in the internal space. For example, providing a conduit at least partially within the internal space of the vessel can include using the desiccant to support the conduit, at least in part, in the internal space. In some cases, venting fluid from the vessel can include venting fluid from the internal space via a fluid pathway defined in part by the desiccant.

In some embodiments, a sample holder includes a vessel having a wall with an outer surface and defining an internal space. The vessel may include a lower portion having a cavity and an upper portion engaged with the lower portion, e.g., by way of a threaded connection, interference fit, bayonet connection, etc. A conduit, such as a capillary tube, may have a distal end positioned in the cavity of the lower portion of the vessel and a proximal end extending from the internal space, e.g., exposed to receive blood or other sample into the conduit. The conduit may extend through the upper portion of the vessel and be configured to receive a blood sample into the proximal end of the conduit, e.g., by capillary action. A cap may be configured to receive the proximal end of the conduit and engage with the upper portion, e.g., by receiving the upper portion into a cavity of the cap. The cap and the upper portion may each include complementary engagement features that are configured to engage with each other to resist rotation of the cap relative to the upper portion. For example, the complementary engagement features may include one or more ribs formed on the upper portion and/or the cap that engage with each other when the upper portion is received into a cavity of the cap. The cap may be movable relative to the upper portion from a first position in which the upper portion is partially received into the cap to a second position in which the upper portion is fully received into the cap, and the complementary engagement features may engage to resist rotation only when the cap is in the second position. The upper portion may be threadedly engaged with the lower portion and the lower portion may be configured to be removed from the upper portion by rotating the cap while the complementary engagement features are engaged so as to rotate the upper portion relative to the lower portion. The cap and vessel may include any additional features described above or otherwise herein, and may do so in any arbitrary combination provided such features are not mutually exclusive.

In some embodiments, a sample holder may include a vessel having a wall with an outer surface and defining an internal space. In some cases, the vessel may include a lower portion and an upper portion. A conduit may have a distal end positioned in the internal space and a proximal end extending from the internal space. The conduit may extend through the upper portion and be configured to receive a blood sample into the proximal end of the conduit. A cap may be configured to receive the proximal end of the conduit and engage with the upper portion, e.g., by inserting a part of the upper portion into a cavity of the cap. A stand may be configured to removably receive the lower portion of the vessel and support the vessel on a surface in at least two different orientations, e.g., such that the conduit and/or vessel are oriented with a longitudinal axis along a vertical direction and/or a horizontal direction. In some cases, the stand may be configured to be grasped by a user and permit the user to manipulate the vessel for collection of a blood sample by the conduit. In some examples, the stand and the vessel may be configured to engage to resist rotation of the vessel relative to the stand about a longitudinal axis of the vessel, e.g., so that a cap or other portion engaged with part of the vessel can be rotated and removed from the vessel. The sample holder may include any additional features described above or otherwise herein, and may do so in any arbitrary combination provided such features are not mutually exclusive.

Other advantages and novel features of the invention will become apparent from the following detailed description of various non-limiting embodiments when considered in conjunction with the accompanying figures and claims.

BRIEF DESCRIPTION OF THE DRAWINGS

Aspects of the invention are described with reference to the following drawings in which numerals reference like elements, and wherein.

DETAILED DESCRIPTION

It should be understood that aspects of the disclosure are described herein with reference to certain illustrative embodiments and the figures. The illustrative embodiments described herein are not necessarily intended to show all aspects of the disclosure, but rather are used to describe a few illustrative embodiments. Thus, aspects of the disclosure are not intended to be construed narrowly in view of the illustrative embodiments. In addition, aspects of the disclosure may be used alone or in any suitable combination with other aspects of the disclosure. For example, embodiments are described in which a desiccant is used to support a conduit in a vessel, in which a vent employed to vent gas from the sample holder is sealed or covered by a cap, and in which a cap engages with a vessel to create a pressure to drive a sample in the conduit to flow into the vessel. These features can be employed together in a sample holder, or can be used separately and without one or more of the others. This is just one example, and to the extent not mutually exclusive, other features described herein can be employed together or separately in various embodiments.

Figure 1:
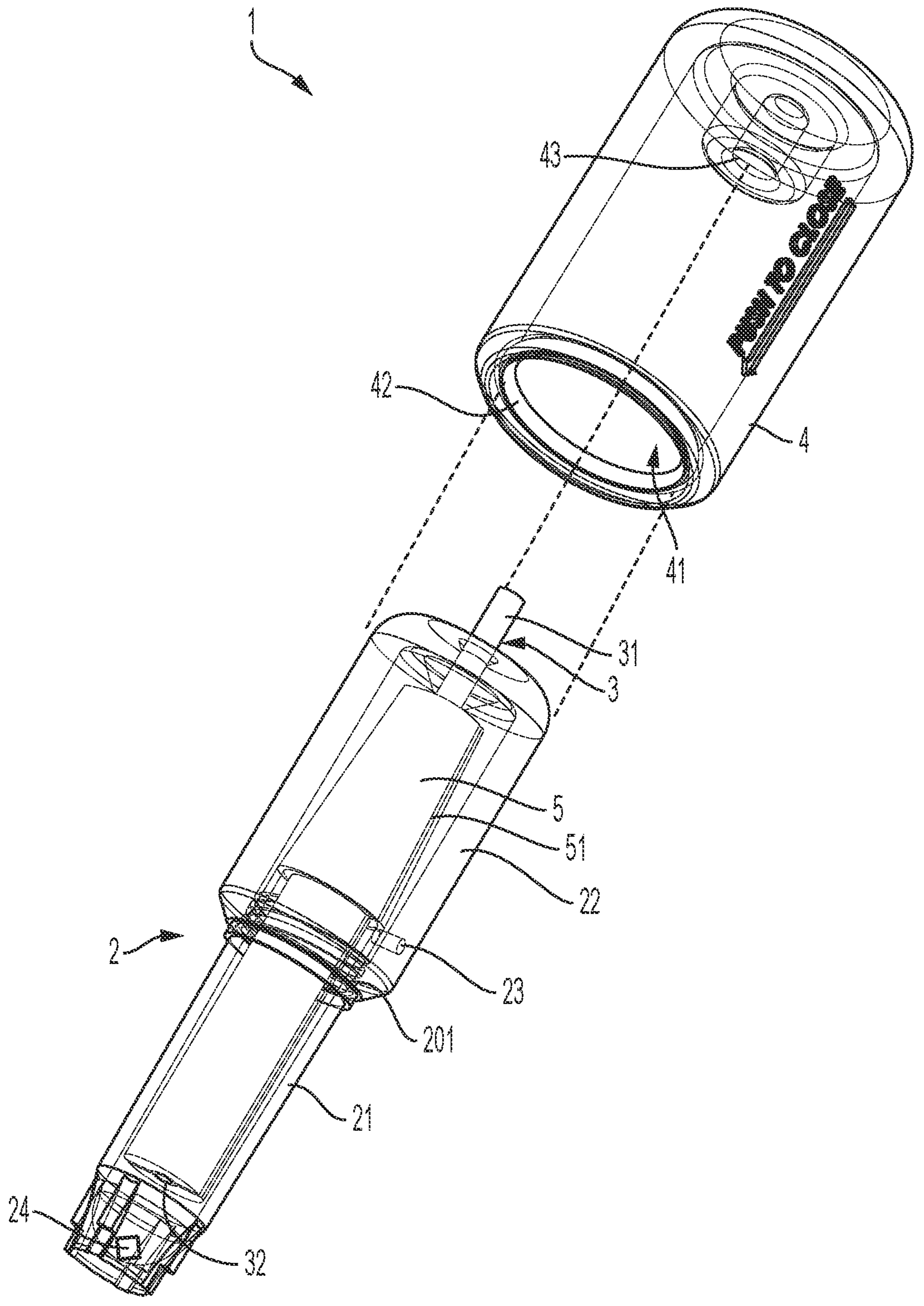
FIG. 1 is perspective view of a sample holder vessel in an illustrative embodiment.

FIG. 1 shows an illustrative embodiment of a sample holder 1 that includes a vessel 2 and a cap 4 that can engage with the vessel 2, e.g., to enclose an internal space of the vessel 2 for storage of a sample in the vessel 2. In some embodiments, the cap 4 can be attached to the vessel 2 by a tether, e.g., to help ensure that the cap 4 is not lost when removed from the vessel 2. The tether can include a string, cord, elastic band or other component that has opposite ends attached to the vessel 2 and the cap 4, respectively. For example, the tether can have a pair of rings at opposite ends of a central elongated element and the rings can be respectively engaged (e.g., by friction fit) over a portion of the vessel 2 and cap 4. However, a tether is not required, e.g., in some cases it may be preferable to separately package or otherwise provide the vessel 2 and cap 4. In some cases, the sample holder 1 includes a conduit 3 that is configured to receive a liquid sample into the tube 3, e.g., by contacting the liquid material with a proximal end 31 of the conduit 3. In some embodiments, capillary action can draw the liquid material into the conduit 3, and the liquid material may flow into the tube 3 so as to fill the tube 3 from the proximal end 31 to the distal end 32. For example, the conduit 3 can include a capillary tube configured to draw a liquid sample, such as liquid blood, into the conduit 3 by contacting the liquid with the proximal end 31. In some cases, the conduit 3 can include a wick or other component that can receive a liquid sample (e.g., by wetting, capillary action, etc.). In some embodiments, a wick or other component can be contained within an outer tube or conduit. The conduit 3 need not necessarily be configured to receive a sample by capillary action. Instead, the conduit 3 can receive a liquid sample by applying negative pressure to the distal end 32 of the conduit 3 (e.g., using a pump bulb or other vacuum source connected to the vessel or conduit 3), or by applying positive pressure to urge the liquid sample to flow into the conduit 3 (e.g., by pipette). For example, the cap 4 could be provided with liquid sample and the cap 4 engaged with the vessel 2 so the sample in the cap 4 is driven into the conduit 3. In some cases, the conduit 3 can be configured to collect a particular type of sample, such as liquid blood or other material, and the conduit 3 can be configured to collect a sample having a desired volume. For example, the conduit 3 can be configured to be completely filled with a liquid sample material and to have a particular internal volume so that the collected sample has a desired total volume. This arrangement can avoid any need for a user to measure sample material or otherwise take steps to collect a particular sample volume. In some cases, the conduit 3 can be visualized by a user, e.g., upper and/or lower portions of the conduit 3 can be visualized so the user can see the extent to which the conduit 3 is filled with sample. This can permit a user to confirm a volume of sample has been received by the conduit 3.

The conduit 3 can be supported or otherwise held in the vessel 2, e.g., so that a user can hold and manipulate the vessel 2 to contact the proximal end 31 of the conduit 3 to a sample material. This may help ease use of the sample holder 1 since the user need not handle a relatively small and delicate conduit 3. It may also help prevent contamination of a sample since a user may be less likely to touch or otherwise contact the conduit 3, e.g., at the proximal end 31. A portion of the conduit 3 can protrude from the vessel 2, e.g., having a sufficient length to permit suitable contacting of the proximal end 31 with a liquid sample material. In some cases, the conduit 3 can be supported in the vessel 2 by a conduit holder 5, which can be part of the vessel 2 and/or a separate component that is engaged with the vessel 2. The conduit holder 5 can engage with the conduit 3 (e.g., the conduit 3 can pass through an opening of the conduit holder 5) and can engage with the vessel 2 (e.g., the conduit holder 5 can engage with the inner wall of the vessel 2) to secure the conduit holder 5 and conduit 3 in place. The conduit 3 can be supported so that the distal end 32 of the conduit 3 is positioned in a desired way in the vessel 2, e.g., so that the distal end 32 is positioned above a bottom of the vessel 2. This can help prevent the conduit 3 from drawing liquid material into the conduit 3 from the distal end 32, e.g., because the distal end 32 can be positioned above liquid material in the vessel 2. In some embodiments, the vessel 2 and conduit holder 5 can be configured so that a user can see the conduit 3, e.g., while providing a sample into the conduit 3. For example, the conduit holder 5 can include a slot or other opening to permit the user to see the conduit 3 and/or the conduit holder 5 and the vessel 2 can include a transparent material or window that permits the user to see the conduit 3. This can help a user determine that the conduit 3 is full or otherwise has a suitable sample volume, e.g., preventing the user from overdrawing a sample. In some cases, the conduit holder 5 can include a desiccant material, e.g., suitable for drying a blood or other liquid sample held in the vessel 2. A desiccant can include a molecular sieve such as a zeolite, a silica gel, or other suitable material for drying blood or other liquid samples. In some embodiments, the conduit holder 5 can be made entirely of desiccant material. The conduit holder 5 including desiccant can be positioned in the vessel 2 so that the desiccant is suitably close to a blood or other liquid sample held in the vessel 2, e.g., at the bottom of the vessel 2. The sample holder 1 can include an immobilizer 24 such as a chemical material and/or structure in the internal space of the vessel 2 (e.g., at the bottom of the vessel 2) to immobilize or otherwise act on the blood or other sample, e.g., to help preserve or otherwise treat the sample for drying or later use. For example, the immobilizer 24 can increase a viscosity of a sample, enhance the sample's ability to adhere to the vessel 2 surface, capture portions of the sample in voids or other spaces (e.g., by surface tension, wetting or absorbance features), etc.

Figure 2:
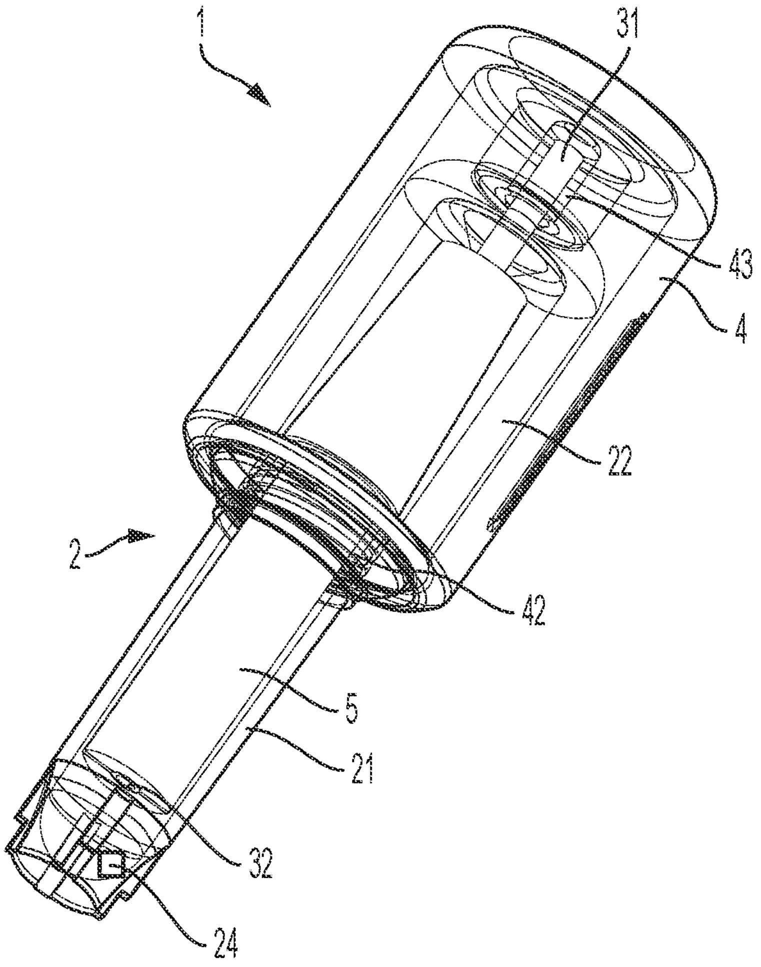
FIG. 2 is a perspective view of the FIG. 1 sample holder with a cap engaged with a vessel of the sample holder.

After a blood or other sample is drawn into or otherwise provided to the conduit 3, the cap 4 can be engaged with the vessel 2 and moved from a first position (e.g., where a seal 42 of the cap 4 initially engages with the upper end of the vessel 2) toward a second position (e.g., such as that shown in FIG. 2 where a portion of the vessel 2 is fully received into the cap). In some cases, the cap 4 can have a cavity 41 configured to receive at least a portion of the vessel 2 and the proximal end 31 of the conduit 3. When engaging the cap 4 with the vessel 2, the vessel 2 can be oriented vertically, e.g., so that the proximal end 31 of the conduit 3 is positioned above the distal end 32 and the bottom of the vessel 2. The cap 4 and vessel 2 can be configured so that when the cap 4 is moved from the first position toward the second position, positive pressure is created in the cavity 41. For example, the seal 42 (such as an o-ring) on the cap 4 can engage with the vessel 2 to create an airtight seal between the cap 4 and the vessel 2. As the vessel 2 is moved into the cavity 41 of the cap 4, gas in the cavity 41 (such as air) is put under pressure because of the reducing gas volume of the cavity 41. The positive pressure in the cavity 41 can cause gas to flow from the cavity 41 into the proximal end 31 of the conduit 3, thereby forcing a blood or other sample in the tube 3 to flow toward the distal end 32 and into the bottom of the vessel 2. While in some embodiments the cap 4 includes a seal 42 to engage with the vessel 2, other arrangements are possible. For example, the cap 4 and vessel 2 can engage with a close or interference fit, the vessel 2 can have one or more seals that engage with an inner wall of the cavity 41 of the cap 4, and so on. In some cases, the vessel 2 and cap 4 can be configured to cause a volume of gas that is larger than the volume of the conduit 3 to flow through the conduit 3 as the cap 4 is moved from the first position toward the second position. This can help ensure that a sample in the conduit 3 is completely discharged into the vessel 2. In some cases, the volume of gas moved through the conduit 3 can be two or more times the volume of the conduit, e.g., 3, 4, 5, 10 or more times the volume of the conduit 3. In cases where the conduit 3 includes a wick or other element that receives a sample by wetting, capillary action contained within an outer tube or conduit, relatively high volumes of gas moved through the conduit 3 by the cap 4 can assist in ensuring a suitable amount of sample is discharged from the conduit 3.

Movement of a blood or other sample and/or gas from the cavity 41 out of the distal end 32 of the conduit 3 will tend to increase the pressure in the internal space of the vessel 2. In some embodiments, the sample holder 1 includes a fluid pathway by which fluid can exit the internal space of the vessel 2 as the cap 4 is moved from the first position toward the second position. For example, the vessel 2 can include an opening 23 that extends through a wall of the vessel 2 via which fluid can exit the internal space of the vessel 2. As a sample is drawn into the conduit 3, any pressure created in the internal space of the vessel 2 because of movement of the liquid sample into the conduit 3 can be vented through the opening 23. In addition, as a cap 4 is engaged with the vessel 2 and moved to urge the liquid sample in the conduit 2 into the internal space of the vessel 2, any gas pressure in the vessel 2 such as the gas from the cavity 41 used to purge or otherwise move the sample out of the conduit 3 can be vented through the opening 23. Thus, the cap 4 can be employed to move a blood or other sample out of the conduit 3 without excessively pressurizing the internal space of the vessel 2. This may help make movement of the cap 4 from the first position toward the second position relative to the vessel 2 easier, e.g., because internal pressure in the vessel 2 will generally not resist movement of the cap 4 relative to the vessel 2. Similarly, the opening 23 and/or other vent can help make removal of the cap 4 from the vessel 2 easier. In some cases, fluid in the vessel 2, e.g., near the distal end 32 of the conduit 3, can flow toward the opening 23 via a portion of the fluid pathway defined by the conduit holder 5, the vessel 2 or other component. For example, in some embodiments the conduit holder 5 includes a channel 51 that can define a fluid pathway that communicates with the opening 23. Air or other gas can flow along the channel 51 to the opening 23 for venting from the internal space of the vessel 2. In some embodiments, blood or other liquid sample material may not flow along the fluid pathway to the opening 23 or other vent, e.g., because the blood or other liquid sample is held in place by the immobilizer 24. The immobilizer 24 can include a chemical material, e.g., to cause blood to increase in viscosity, and/or a mechanical element such as a cage, filter paper or other component that can hold the blood or other liquid and/or increase a surface area of exposure of the sample to enhance drying and/or help stabilize the sample in the vessel 2. In some embodiments, the sample holder 1 can include a membrane or other component that permits gas to pass the membrane, but not liquid. For example, the fluid pathway in the vessel 2 (e.g., near the channel 51 or opening 23) can include a hydrophobic or other membrane that prevents liquid material from exiting the internal space of the vessel 2, but allows gas to exit.

In some embodiments, after a blood or other sample is discharged from the conduit 3, the opening 23 or other vent can be sealed closed so that a blood or other sample can be contained in a sealed internal space of the vessel 2, e.g., so the blood or other sample is isolated from external environmental conditions such as humidity, oxygen, air, etc. For example, when the cap 4 is moved toward the second position relative to the vessel 2, e.g., as shown in FIG. 2, the seal 42 or other portion of the cap 4 can cover the opening 23, thereby sealing closed the internal space of the vessel 2. In some embodiments, the opening 23 or other vent can be closed in other ways, such as by a plug, sticker or door mounted on the vessel 2. In some cases, the cap 4 can include a recess 43 configured to receive the proximal end 31 of the conduit 3. Receipt of the proximal end 31 by the recess 43 can help support the conduit 3 in the sample holder 1 and/or seal the proximal end 31 closed, e.g., to help prevent a blood or other sample from exiting the proximal end 31. The recess 43 may only seal the proximal end 31 of the conduit 3 when the cap 4 is fully seated on the vessel 2, e.g., in the position shown in FIG. 2. In some embodiments, the internal space of the vessel 2 may be sealed closed except for the conduit 3 and a fluid pathway such as the opening 23 when the cap 4 is disengaged from the vessel 2. For example, when the cap 4 is disengaged from the vessel 2, the internal space of the vessel 2 may be sealed closed except for the conduit 3 and the fluid pathway (e.g., the opening 23). When the cap 4 is engaged with the vessel 4, e.g., so the seal 42 engages with an upper end of the vessel 2, the internal space can be sealed closed except for the opening 23 or other fluid pathway that permits fluid to exit the vessel 2 as the cap 4 is moved toward the second position. When the cap 4 is in the second position, e.g., where the cap 4 covers the opening 23, the internal space can be completely sealed closed. These arrangements can help ensure that a blood or other sample is exposed to potential contaminants or other conditions to a minimal extent.

Figure 3:
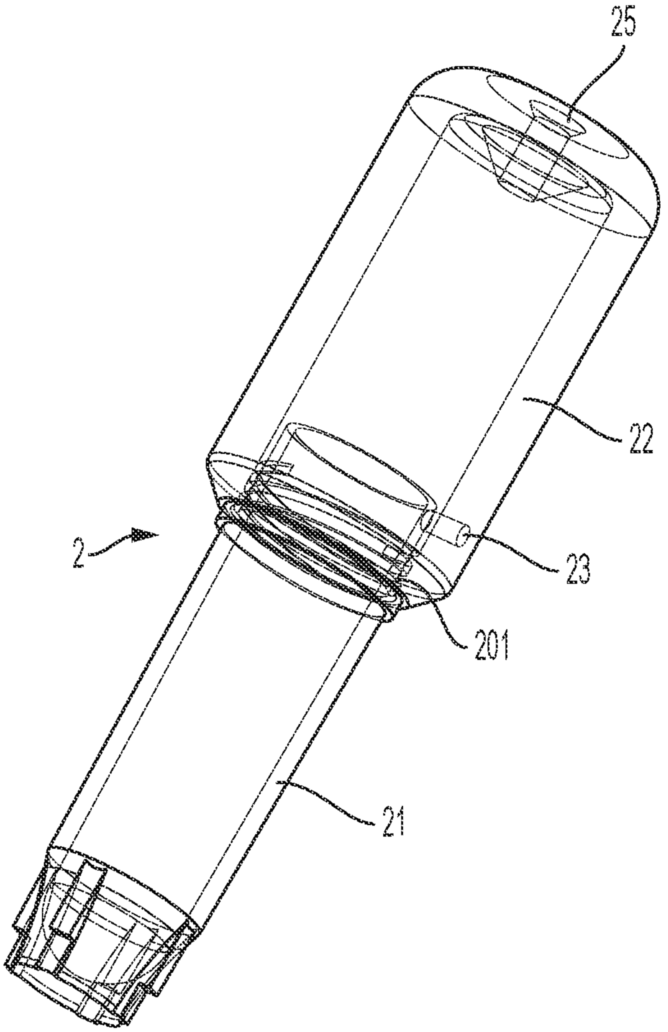
FIG. 3 is perspective view of the vessel of the FIG. 1 sample holder.
Figure 4:
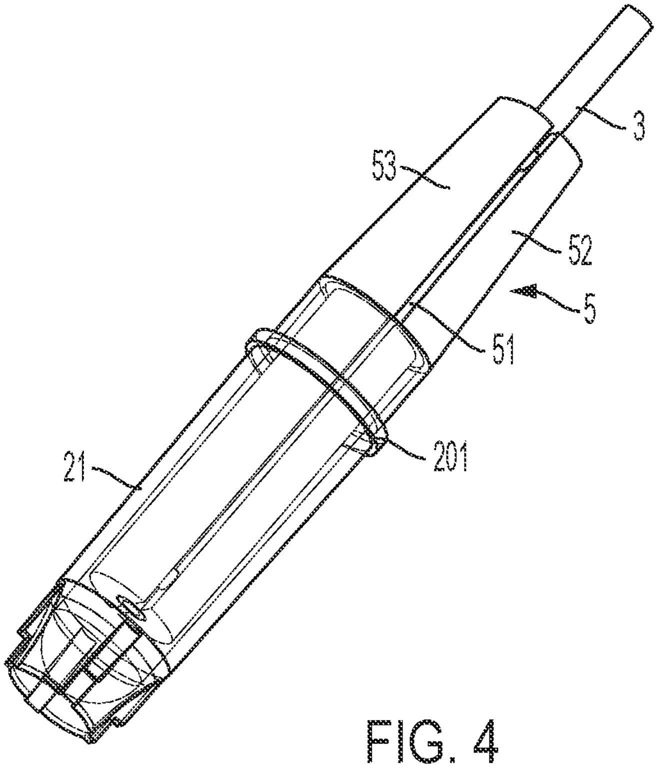
FIG. 4 is a perspective view of the lower vessel portion, holder and conduit of the FIG. 1 sample holder.

In some embodiments, the vessel 2 can have an upper portion 22 that has a different diameter or size than a lower portion of the vessel 2. For example, the upper portion 22 can be tubular in shape and have a larger diameter or other size than the lower portion 21. The larger size of the upper portion 22 can interact with a larger cavity 41 of the cap 4, thereby increasing a volume of air or other gas that is moved through the conduit 3 when the cap 4 is moved from the first to the second position. The smaller size of the lower portion 21 can help contain a blood or other sample in a relatively small volume in the internal space of the vessel 2, which may help improve interaction with an immobilizer 24 or other material and/or with a desiccant in the internal space. For example, a smaller internal volume of the vessel 2 may help a blood sample to dry faster and/or more rapidly in the presence of a desiccant. In some embodiments, the vessel 2 can be made of two or more parts that are joined together. For example, as can be seen in FIG. 3, the upper portion 22 of the vessel 2 may be made of a tubular part that is joined (e.g., by a threaded connection 201 shown, or by an adhesive, interference fit or other connection) to the lower portion 21 which is made of a separate tubular part. This type of arrangement may aid in assembly of the sample holder 1. For example, a conduit holder 5 and conduit 3 can first be inserted into the internal space of the lower portion 21 as shown in FIG. 4, and thereafter the upper portion 22 can be engaged with the lower portion 21 to secure the conduit holder 5 and conduit 3 in place. In some cases, a conduit 3 and conduit holder 5 (where used) may be engaged with the upper portion 22, and then the assembled upper portion 22 and conduit 3 engaged with the lower portion 21. In some cases, the upper portion 22 can include an opening through which the proximal end of the conduit 3 can extend. The conduit 3 can sealingly engage or otherwise engage with the upper portion 22 at the opening 25, e.g., by an adhesive, gasket, friction fit, etc. Thus, the upper portion 22 can include or be part of a conduit holder 5 that supports the conduit 3 in the vessel 2, e.g., the upper portion 22 can engage the conduit 3 at the opening 25 to help support the conduit 3. In some cases, the conduit 3 can fit relatively loosely in the opening 25.

Figure 5:
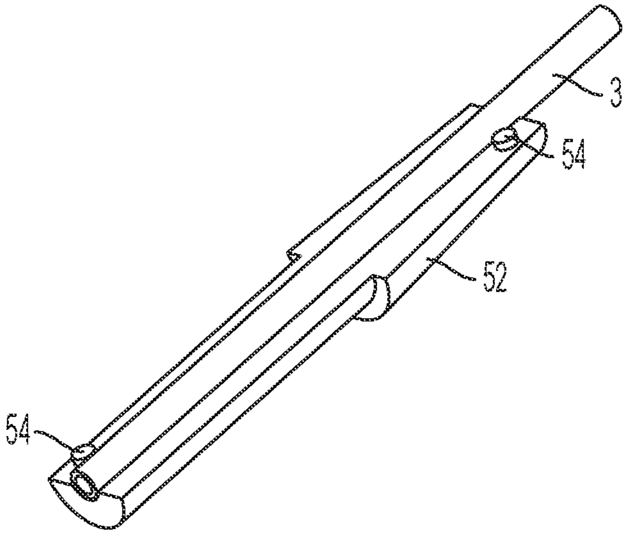
FIG. 5 is a perspective view of a portion of the conduit holder and conduit.

The conduit holder 5 can be configured in different ways. For example, the conduit holder 5 can be arranged so that the conduit 3 passes through a central opening or passageway of the conduit holder 5. For example, as shown in FIG. 4, the conduit holder 5 can include first and second clamshell portions 52, 53 that sandwich the conduit 3. FIG. 5 has the second clamshell portion 53 removed and shows the first clamshell portion 52 and the conduit 3 only. The first clamshell portion 52 includes a groove to receive the conduit 3 and a pair of standoffs 54. The second clamshell portion 53 can be configured in the same way as the first clamshell portion 52 and placed over the conduit 3 to sandwich the conduit 3 between the clamshell portions 52, 53. The standoffs 54 can help prevent the clamshell portions 52, 53 from contacting each other except at the standoff 54 areas. This can help ensure that a channel 51 is defined along the length of the conduit holder 5. The channel 51 can provide different functions, such as enabling a user to visualize the conduit 3 (e.g., where the vessel 2 is made of a transparent material) so that the user can identify whether the conduit 3 holds a blood or other sample or not and/or can confirm that a sample is being drawn into the conduit 3. The channel 51 can also, or alternately, provide a flowpath for gas or other fluid to flow to or from the opening 23 or other vent, e.g., when the cap 4 is moved relative to the vessel 2. The channel 51 can also, or alternately, provide an increased surface area of the conduit holder 5 that is exposed to the internal space of the vessel 2. For example, where the conduit holder 5 is made of or otherwise includes a desiccant, the increased surface area exposed to the internal space can aid in more rapid or complete drying of a blood or other sample. The first and second clamshell portions 52, 53 can fit into the vessel 2 to support the conduit 3 in the vessel 2. For example, the assembled clamshell portions 52, 53 and conduit 3 can fit into the lower portion 21 or upper portion 22 of the vessel 2 so that the clamshell portions 52, 53 engage the inner wall of the lower portion 21 or upper portion 22 with an interference fit or other friction fit to suitably hold the conduit 3 in place. A relatively tight fit of the clamshell portions 52, 53 in the vessel 2 can also provide a clamping force on the conduit 3, thereby helping to ensure the conduit 3 is held securely between the clamshell portions 52, 53. The clamshell portions 52, 53 can define a lower section that is generally cylindrical in shape, or otherwise suitably shaped to fit into the lower portion 21. The clamshell portions 52, 53 can define an upper section that provides a stop, e.g., to engage with a rim of the lower portion 21 so that insertion of the clamshell portions 52, 53 into the lower portion 21 is limited to a desired extent. This can help ensure that the conduit distal end 32 is suitably positioned in the vessel 2. The upper section of the clamshell portions 52, 53 may define a tapered shape, e.g., that is tapered so as to be smaller in size nearer the proximal end 31 of the conduit 3 than in areas further form the proximal end. This may help guide engagement of the upper portion 22 with the lower portion 21. In some cases, the conduit holder 5 can be configured to fill the internal space of the vessel 2 to a desired extent, e.g., to take up 50%, 60%, 70%, 80% or more of the internal space of the vessel 2. This can help reduce the volume of the internal space, which may aid in drying of a blood sample.

Figure 6:
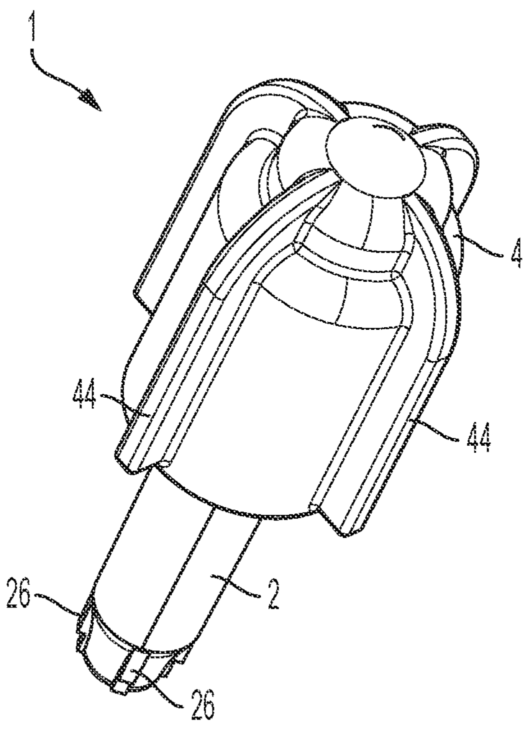
FIG. 6 is a perspective view of a sample holder with a cap engaged with a vessel of the sample holder in which the cap includes engagement features.

In some embodiments, one or more portions of a sample holder may have engagement features, e.g., to help a user rotate or resist rotation of one or more portions of the sample holder or otherwise grasp and manipulate the sample holder, and in some cases the engagement features may be complementary engagement features that are configured to engage with corresponding complementary engagement features on another component, e.g., to help resist rotation of one portion of a sample holder relative to another portion of the sample holder or relative to a separate structure. For example, FIG. 6 shows an illustrative embodiment in which a cap 4 includes engagement features 44, e.g., to help a user grasp and rotate or otherwise manipulate the cap 4 in a desired way. The engagement features 44 may take various forms, such as ribs, fins, knurling, surface roughness, or other structures to aid a user in grasping the cap 4. In some cases, the engagement features 44 may include radially extending elements, such as fins or ribs that extend along all or a part of a length of the cap 4. In some examples, the fins or ribs may extend over part of the sidewall and/or the upper part of the cap 4 as shown in FIG. 6. Any suitable number of fins, ribs, tabs or other engagement features 44 may be provided. As another example, the vessel 2 may include one or more engagement features 26, such as fins, ribs, knurling, surface roughness, or other structures, e.g., to aid a user in grasping the vessel 2. In some cases, such engagement features 26 may be provided on the upper and/or lower portion 22, 21 of the vessel 2. As with engagement features on the cap, the engagement features 26 may extend over part of the sidewall, the upper part and/or the lower part of the vessel 2 as shown in FIG. 6, e.g., the engagement features 26 may extend along a longitudinal axis of the vessel 2, circumferentially around the vessel 2, and/or in other ways. The engagement features 44, 26 may help a user in rotating, sliding or otherwise moving the cap 4 relative to the vessel 2.

Figure 7:
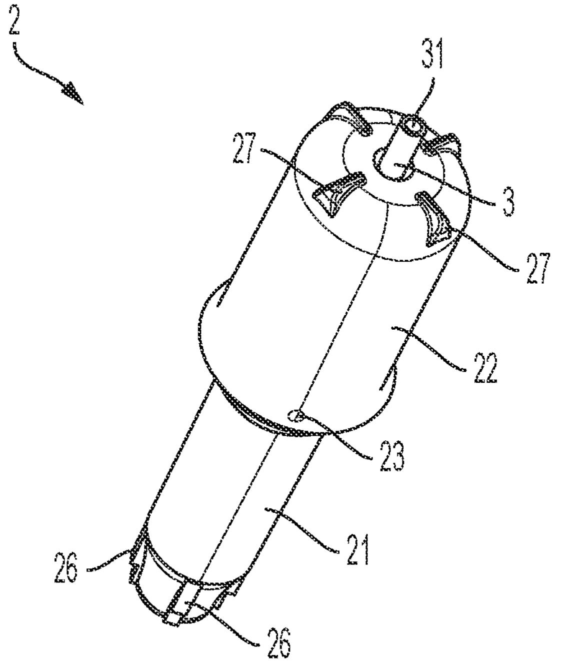
FIG. 7 is a perspective view of the sample holder of FIG. 6 with the cap removed.
Figure 8:
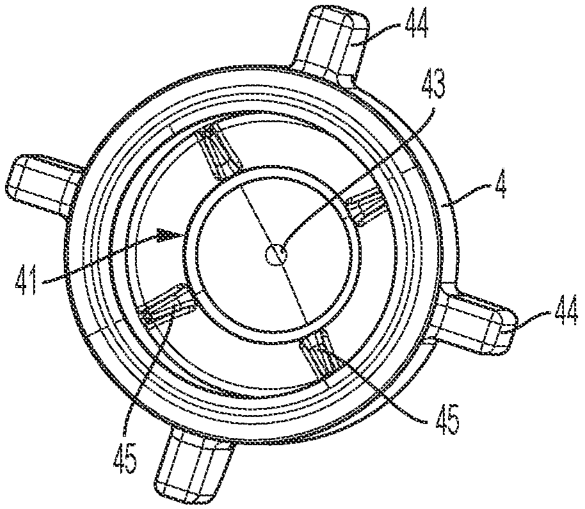
FIG. 8 shows a perspective view of a cavity of the cap of FIG. 6.

In some cases, the engagement features on the sample holder may be complementary with other engagement features on other portions of the sample holder and/or other structures. For example, in some embodiments the vessel 2 and cap 4 may each include complementary engagement features to help resist rotation or other movement of one or more portions of the vessel 2 relative to the cap 4. FIG. 7 shows the cap 4 of FIG. 6 removed and an arrangement in which the upper portion 22 of the vessel 2 includes engagement features 27, e.g., in the form of radially extending ribs, fins, tabs or other suitable features. The engagement features 27 on the upper portion 22 may be complementary to engagement features on the cap 4. For example, FIG. 8 shows a view within the cavity 41 of the cap 4 and illustrates engagement features 45 within the cavity 41 that are configured to engage with the engagement features 27 on the upper portion 22, e.g., to help resist rotation of the cap 4 relative to the upper portion 22. In some cases, the engagement features 27, 45 may only engage when the upper portion 22 is fully received into the cavity 41 or at least received to a threshold extent by the cap 4. In some cases, the engagement features 27, 45 may be configured to engage when any part of the upper portion 22 is received in the cavity 41, e.g., the engagement features may include corresponding splines and grooves on the cap 4 and upper portion 22 that extend longitudinally along the cap 4 and upper portion 22. In some cases, engagement of the engagement features 27, 45 with each other may aid in removing the upper portion 22 from the lower portion 21. For example, in embodiments where the upper and lower portions 22, 21 are threadedly engaged, engagement of the engagement features 27, 45 may permit a user to rotate the cap 4, thereby causing the upper portion 22 to rotate with the cap 4. If the lower portion 21 is held stationary relative to the upper portion 22, e.g., by a user grasping the engagement features 26 on the lower portion 21, the upper and lower portions 22, 21 may be rotated relative to each other so as to disengage their threaded coupling and permit the upper portion 22 to be removed from the lower portion 21.

Figure 9:
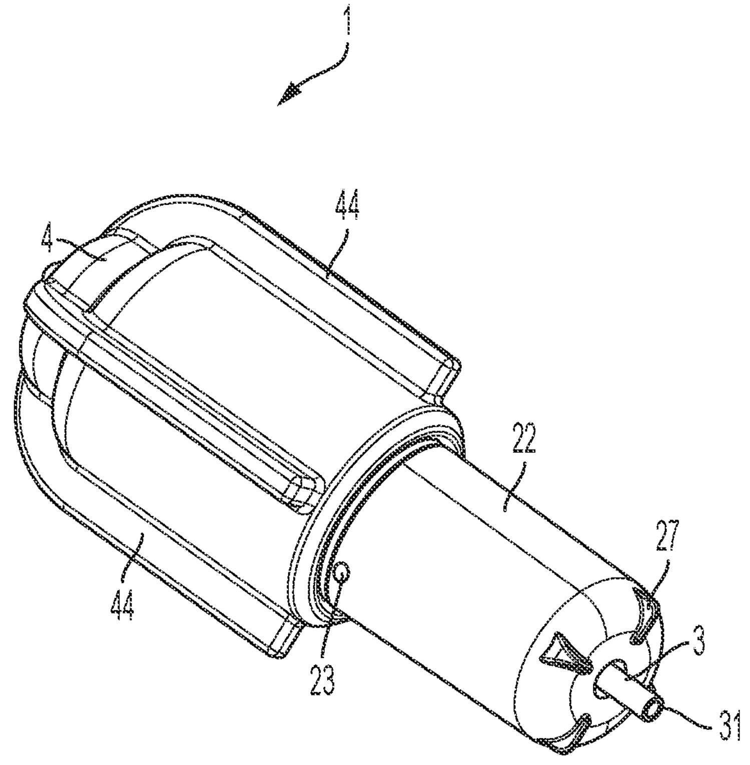
FIG. 9 shows the sample holder of FIGS. 6-8 with the cap removed.

In some embodiments, a cap may be configured to permit a user to manipulate a vessel for collecting a sample and/or to support the vessel on a surface. For example, FIG. 9 shows the sample holder 1 of FIGS. 6-8 with the cap 4 removed from the upper portion 22 and arranged to receive the lower portion 21 so that the proximal end 31 of the conduit 3 is exposed. The cap 4, which may be larger in size than the lower portion 21, may provide a user with a larger or otherwise more effective gripping area than the lower portion 21, e.g., so the user can more easily grasp and manipulate the vessel 2 to collect a blood sample. In some cases, the cap 4 may be configured to support the vessel 2 on a surface, such as a countertop, so that the vessel 2, and particularly the upper portion 22 and the proximal end 31 of the conduit 3, are positioned above the surface on which the cap 4 is placed. As an example, the cap 4 and engaged vessel 2 may be placed on the surface in a horizontal orientation, e.g., such that the conduit 3 is oriented horizontally. This may allow a user to prepare the sample holder 1 for sample collection and place the sample holder 1 on a surface while other actions are taken, such as piercing a subject's skin to produce a blood droplet for collection. Engagement features 44 on the cap 4 may help resist rolling or other movement of the sample holder 1 on the surface. In some cases, the cap 4 may be configured to support the vessel 2 in other orientations, such as a vertical orientation in which the conduit 3 is oriented vertically with the proximal end 31 of the conduit 3 arranged above the distal end 32 of the conduit 3. For example, an end of the cap 4 may have a flat or otherwise configured surface to permit the cap 4 and vessel 2 to be placed on a surface so the vessel 2 extends upwardly from the cap 4 without assistance from a user or other support. After collection of a sample in the conduit 3, the user may remove the cap 4 from the lower portion 21 and place the cap 4 on the upper portion 22, e.g., to move the sample from the conduit 3 into the lower portion 21 and seal the internal space of the vessel 2 closed. Note that the vessel 2 and cap 4 may include any suitable features described herein in combination with those of FIGS. 6-9, e.g., such that movement of the cap relative to the vessel from a first position to a second position causes movement of a blood sample from a conduit into the vessel, etc. As further examples in this regard, the vessel 2 may include a conduit holder 5 or not (e.g., may support the conduit 3 itself), may include a desiccant or not, and so on.

Figure 10:
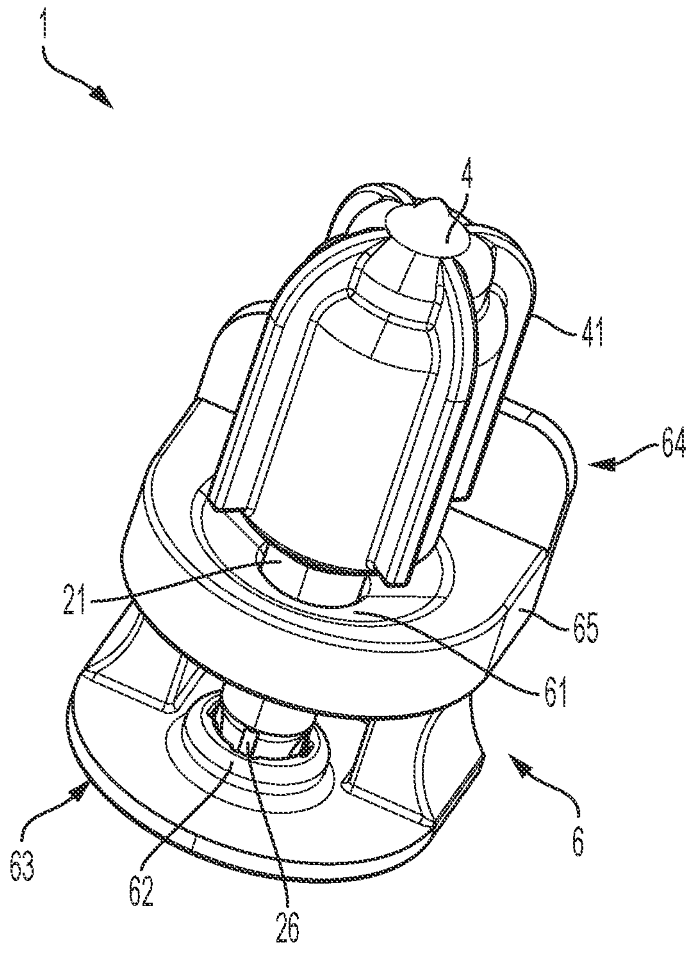
FIG. 10 is a perspective view of the FIG. 6 sample holder received by a stand.

In some cases, a sample holder may include a stand or other support for a vessel, e.g., that can support the vessel in two or more orientations. Such a stand may aid a user in manipulating, securing, or otherwise holding or using the sample holder during use. For example, FIG. 10 shows an embodiment in which a vessel 2 is received and held by a stand 6. The stand 6 can be configured in different ways to receive and hold a vessel 2, e.g., having an opening or cavity 61 to receive at least a portion of the vessel 2. For example, the lower portion 21 of a vessel 2 can be received into the opening 61, e.g., so that the vessel 2 can be held in an upright orientation on a surface without aid from a user. In such a case, a base 63 of the stand 6 can be placed on the surface and can be configured to hold the stand 6 and vessel 2 in an upright orientation on the surface. In some cases, the stand 6 can engage the vessel 2, e.g., so that movement of the vessel 2 relative to the stand 6 in one or more directions is resisted. For example, in some cases the stand 6 may engage with engagement features 26 on the vessel 2 to help resist rotation and/or longitudinal movement of the vessel 2 relative to the stand 6. FIG. 10 shows an illustrative embodiment in which the stand 6 includes one or more recesses 62 configured to engage with the engagement features 26 on the lower portion of the vessel 2, e.g., to resist rotation of the lower portion 26 relative to the stand 6. Engagement features on the stand 6 may take any suitable form and may be complementary to engagement features on the vessel 2. For example, in FIG. 10 the lower portion 21 includes engagement features 26 in the form of radially extending ribs near a bottom of the vessel 2. Thus, engagement features on the stand 6 may include one or more recesses to receive and engage with the ribs on the vessel 2. However, the engagement features may be configured in other ways, e.g., recesses on the vessel 2 may be engaged by ribs or tabs on the stand 6, and so on. In some cases, the stand 6 may frictionally engage with the vessel 2, e.g., to resist rotational and/or longitudinal movement of the vessel 2 relative to the stand 6. For example, a portion of the stand 6 at the opening 61 or other area may frictionally engage the vessel 2 so the vessel 2 cannot be easily inserted into and/or removed from the opening 61. This may assist in ensuring the vessel 2 and stand 6 are not separated in an unwanted or unintentional way.

Figure 11:
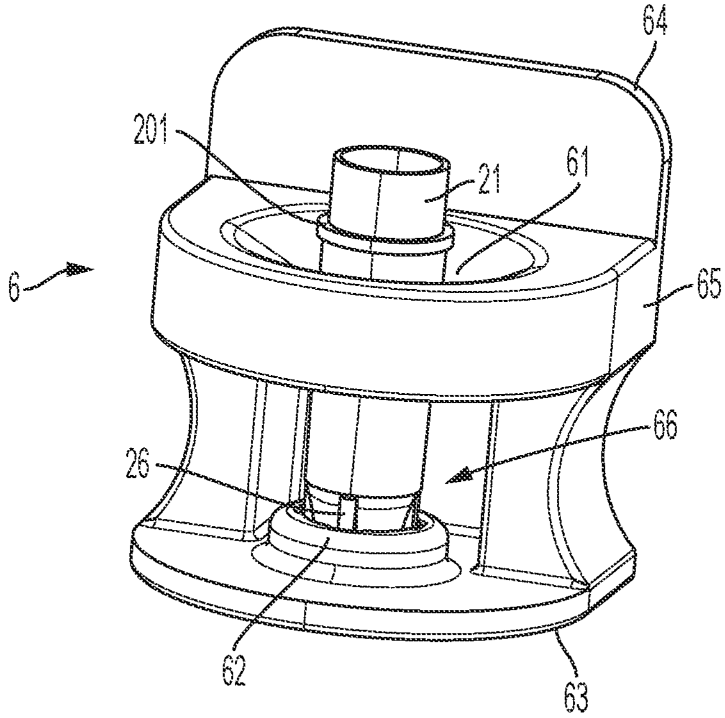
FIG. 11 shows a portion of a vessel received by a stand like that in FIG. 10.
Figure 12:
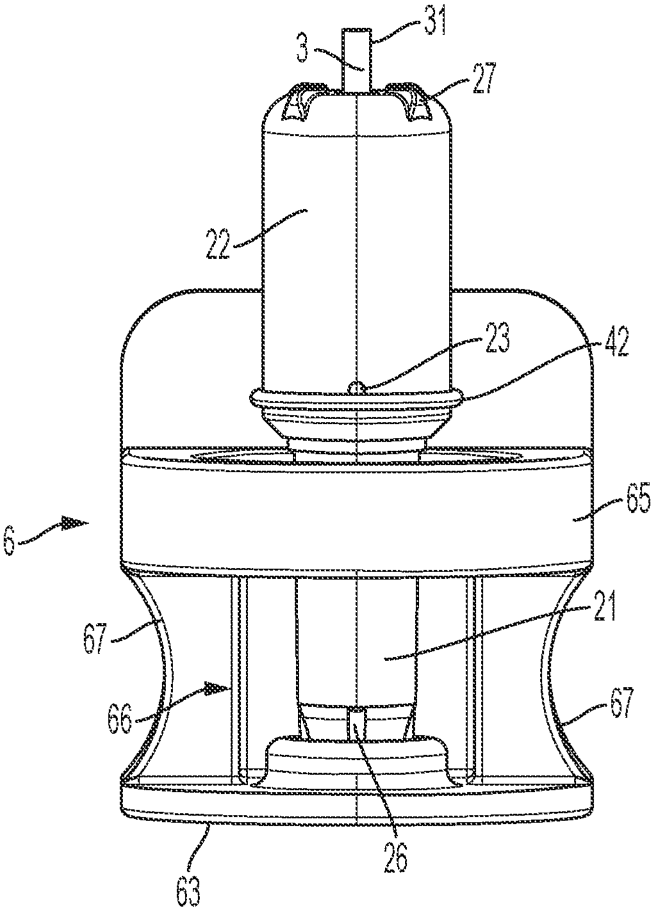
FIG. 12 is a front view a vessel of a sample holder received by a stand like that in FIG. 10.

Engagement of the stand 6 with the vessel 2 may aid in disassembly and/or assembly of the sample holder, collection of sample material, treatment of sample material in the vessel, etc. For example, in some cases, the stand 6 may engage the lower portion 21 of the vessel to resist relative rotation of the lower portion 21 relative to the stand 6, e.g., by engaging the engagement features 26 with the recess(es) 62. However, the upper portion 22 of the vessel 2 and/or the cap 4 may not be directly engaged with the stand, e.g., such that the cap 4 and upper portion 22 can be rotated relative to the lower portion 21 and the stand 6. As a result, a user can rotate the cap 4 and thereby rotate the upper portion 22 relative to the lower portion 21 and the stand, e.g., allowing the user to disengage and/or engage the upper and lower portions 22, 21 from each other. FIG. 11 shows an example where the cap 4 and upper portion 22 are removed from the lower portion 21, e.g., by rotating the cap 4 and upper portion 22 to disengage a threaded coupling 201 of the lower portion 21 from the upper portion 22. This can expose the internal space of the lower portion 21, e.g., permitting a user to access a sample in the lower portion and/or to add material such as treatment reagents to the lower portion. As noted above, the stand 6 may support the lower portion 21 on a surface without assistance from a user, e.g., by resting the base 63 on the surface. In some cases, removal of the upper portion 22 from the lower portion 21 may remove a conduit 3 and/or holder 5 (where present) as can be seen in FIG. 11, e.g., the conduit 3 and/or holder 5 may be secured to the upper portion 22. Alternately, removal of the upper portion 22 from the lower portion 21 may leave the conduit 3 and/or holder 5 in place in the lower portion 21, e.g., as can be seen in FIG. 12. FIG. 12 also shows a position of the seal 42 when the cap 4 is positioned to fully receive the upper portion 22 into the cavity 41. That is, the seal 42 is positioned below the opening 23 so that the internal space of the vessel 2 can be sealed closed as discussed above. Note that the seal 42 is typically carried by the cap 4, but in some cases, a seal 42 may be provided as shown in FIG. 12, e.g., to aid in suitably sealing the cap 4 and vessel 2 to enclose the internal space when the cap 4 is fully engaged onto the vessel 2.

In some cases, the stand 6 may be configured to permit visualization or other observation of at least a portion of the vessel 2 when the vessel 2 is held by the stand 6. This may, for example, permit a user to confirm that a sample has been properly received into the vessel 2, e.g., after a cap 4 has been placed onto the vessel 2 and moved to drive a sample from the conduit 3 to the vessel 2. For example, the stand 6 may be transparent and/or include a window 66 so a part of the lower portion 21 can be observed by a user and/or optical detector. The window 66 may be formed as a cavity or opening in a portion of the stand 6, e.g., between the base 63 and a collar 65 that includes a part of the opening 61 into which the vessel 2 is received. In some cases, the collar 65 may have a tapered or concave portion around the opening 61, e.g., to help guide movement of a vessel 2 into the opening 61.

Figure 13:
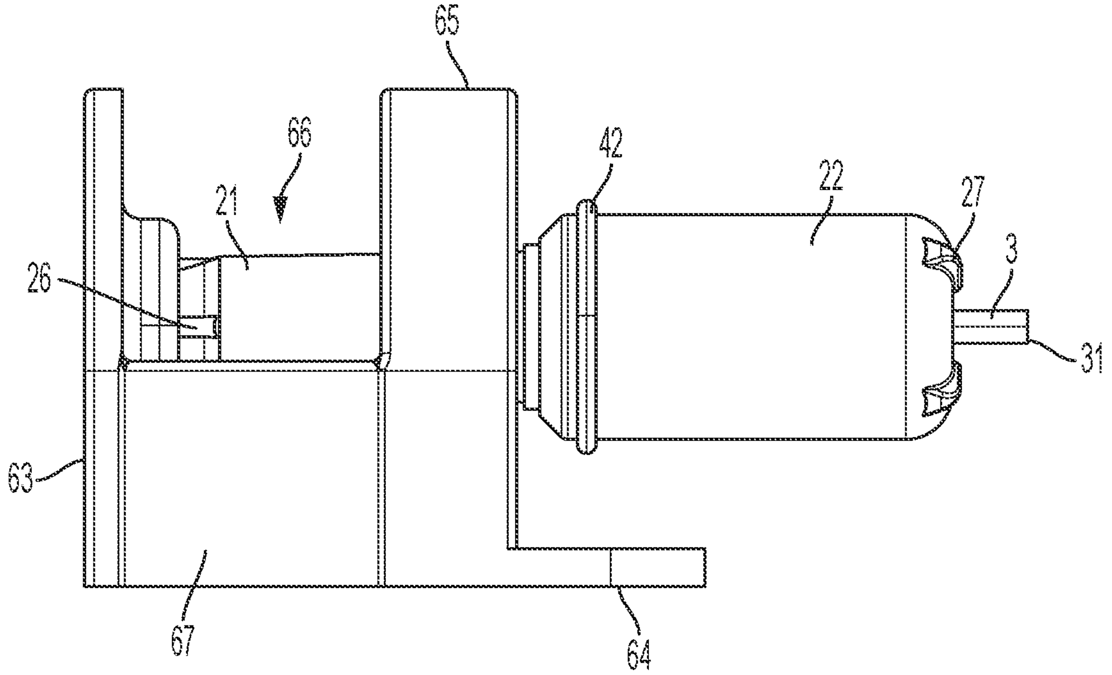
FIG. 13 is a side view a vessel and stand in a horizontal orientation.

In some embodiments, the stand may be configured to aid a user in grasping and manipulating the stand 6 and an attached sample holder 1. For example, the stand 6 may be sized and shaped to be comfortably and accurately manipulated by hand by a user. Features of the stand 6 to assist in manipulation can vary as desired; in some cases the stand 6 may include finger grips 67, e.g., one or more concave portions that are sized and shaped to permit a user's fingers to hold the stand 6. In some cases, the finger grips 67 can be configured for gripping between a forefinger and thumb; in some cases, the finger grips 67 can be configured to be positioned between adjacent fingers, e.g., so portions of an index and middle finger are engaged at the finger grips 67. This may permit a user to position the proximal end 31 of the conduit 3 at a sample source to provide a sample into the conduit 3, e.g., by capillary action. As noted above, the stand 6 may be configured to support the vessel 2 in multiple orientations, whether while the stand 6 is held by a user or the stand 6 is placed on a surface. One such orientation (e.g., a vertical orientation in which the conduit 3 is oriented vertically) is shown in FIG. 12 where the base 63 of the stand 6 may be placed on a surface such as a counter top to support the vessel 2 without user or other assistance. Another possible orientation (e.g., a horizontal orientation in which the conduit 3 is oriented horizontally) is shown in FIG. 13 where the stand 6 may be placed on its rear wall 64 on a surface such as a countertop to support the vessel 2 without user or other assistance. Both orientations may be useful for different purposes, such as harvesting a sample, removing a cap from or placing a cap on a vessel, or others.

Figure 14:
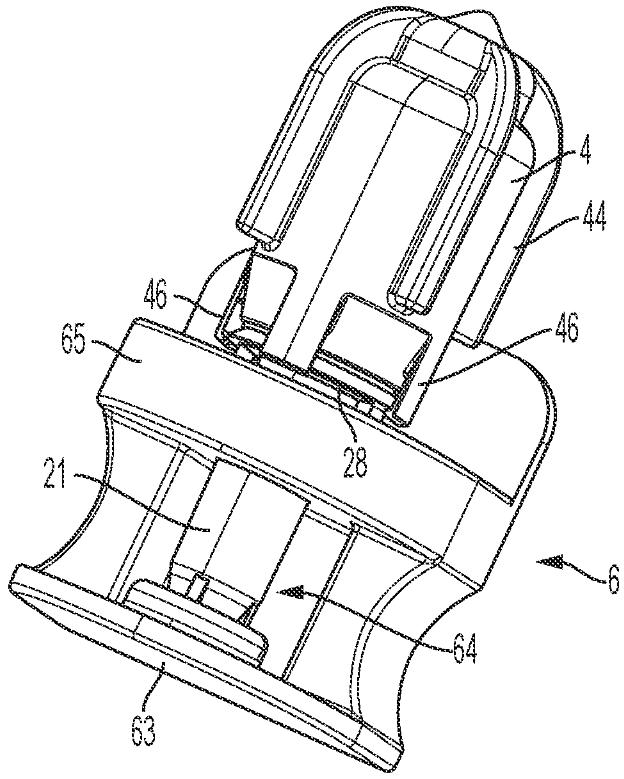
FIG. 14 is a perspective view of a sample holder and stand in which a cap has features to lock onto a vessel.
Figure 15:
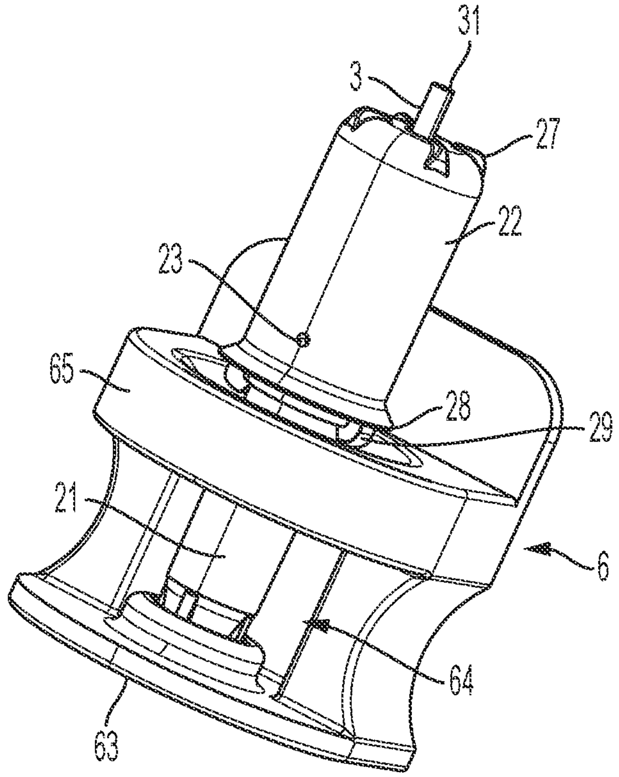
FIG. 15 is a perspective view of a vessel having an upper portion with features to lock onto a lower portion of the vessel.

In some embodiments, a cap can be configured to lock onto a vessel, e.g., so the cap cannot be removed from the vessel or from a portion of the vessel. Such a configuration may help reduce contamination of a sample after the sample has been collected and/or confirm that a sample has not been exposed to an external environment since being collected. FIGS. 14 and 15 show an arrangement in which a cap 4 is configured to lock onto a vessel 2, either removably or non-removably. In some embodiments, a cap 4 may include one or more latches 46 configured to engage with a portion of a vessel 2, e.g., such that once the latches 46 are engaged with the vessel 2, the cap 4 cannot be removed without disengaging the latches 46. In some cases, the latches 46 may be configured as hooks that extend downwardly along one or more sides of the cap 4, e.g., downwardly from a bottom edge of the cap 4. The latches 46 may be configured to resiliently bend outwardly, e.g., so that lower hook portions of the latches 46 move radially away from a longitudinal axis of the vessel 2. In some cases, such outward movement of the hook portions can be caused by the hook portions contacting a part of the vessel 2, e.g., downwardly and outwardly flared or extending surfaces of a ledge 28 on the upper portion 22 of a vessel 2. Thus, as the cap 4 is pressed downwardly onto the upper portion 22 of a vessel 2, e.g., to move a sample in a conduit 3 into the lower portion 21, the lowermost surfaces of the hooks on the latches 46 may contact the ledge 28 to bow or flex outwardly until the hooks are positioned below the ledge 28. With the hooks positioned below the ledge 28, the latches 46 can bend inwardly, e.g., due to a resilient or elastic recovery, so the hooks engage with the ledge 28. With the hooks engaged with the ledge 28, the cap 4 may not be removed without disengaging the latches 46 from the ledge 28, e.g., by exerting suitable upward force on the cap 4 and/or bending the latches to disengage the hooks from the ledge 28. As described above, the cap 4 and upper portion 22 may include complementary engagement features 27, 45, e.g., so the cap 4 and upper portion 22 can be rotated relative to the lower portion 21. In some cases, the upper portion 22 may engage the lower portion 21 in a way similar to that between the cap 4 and upper portion 22 in FIGS. 14 and 15, e.g., the upper portion 22 may include one or more latches 29 (see FIG. 15)

that are configured to engage with a corresponding ledge or other part of the lower portion 21 to secure the upper and lower portions 22, 21 together. The upper and lower portions 22, 21 and/or the cap 4 and upper portion 22 may be disengaged using a suitable tool, e.g., to disengages the latches from corresponding ledge features, applying suitably large force and/or by cutting or otherwise damaging the latches. Thus, a tamper evident securement between the upper and lower portions and/or the cap and vessel may be provided.

Figure 16:
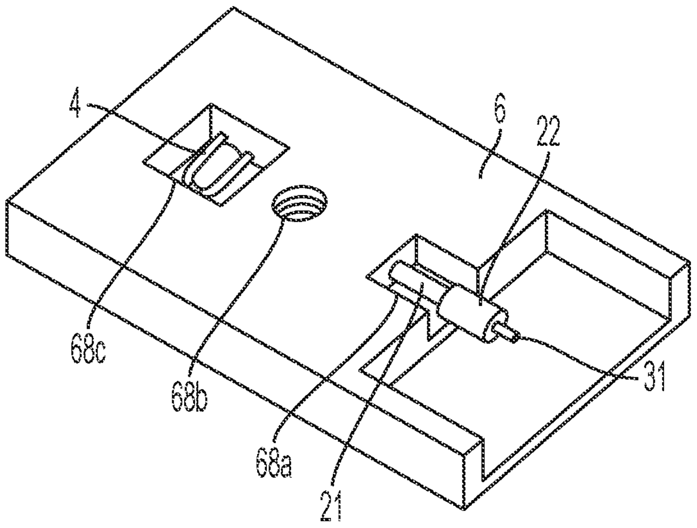
FIG. 16 is a perspective view of a sample holder and a stand in another illustrative embodiment.

While the stand illustrated in the drawings has a particular configuration, any suitable arrangement may be employed for a stand or other support for a sample holder. For example, a stand may be configured as a tray, e.g., a rectangular plate or structure that includes one or more recesses to receive and hold a vessel and/or cap in one or more orientations, such as vertical and horizontal orientations. FIG. 16 shows an illustrative arrangement for a stand 6 configured to support one or more portions of a sample holder 1, e.g., a sample holder arranged like that in FIGS. 1-15. For example, the stand 6 can be configured as a tray having one or more cavities or other support features 68 (such as clips, clamps, frictional elements, etc.) to support portions of a sample holder 1. In some cases, a stand 6 can include a cavity 68*a* configured to support a vessel 2 in a horizontal orientation. In some arrangements, the vessel 2 can be supported by the cavity 68*a* so that a proximal end 31 of the conduit 3 is exposed, e.g., so a blood or other sample can be positioned near the proximal end 31 for harvesting of the sample. In some cases, a cap 4 may be positioned over the upper portion 22 of the vessel 2 while the vessel 2 is held in the cavity 68*a*, e.g., by frictional engagement between the cavity 68*a* and the vessel 2. The cap 4 can be removed, e.g., and placed in another cavity or other support feature 68*c* for the cap 4, to expose the proximal end 31 of the conduit 3. After sample collection, the cap 4 may be replaced on the upper portion 22 and the vessel 2 may remain in the cavity 68*a*. In some cases, the stand 6 may include another cavity or other support feature 68*b* configured to support the vessel 2 in an upright position, e.g., so the proximal end 31 is exposed at an uppermost part of the vessel 2. For example, the vessel 2 may be removed from the cavity 68*a* and placed in the cavity 68*b* for sample collection or preparation for sample collection. After sample collection, the vessel 2 may be supported in the cavity 6*b* and the cap 4 (e.g., after being retrieved from the cavity 68*c*) placed on the upper portion 22 of the vessel. Thereafter, the vessel 2 and cap 4 may be placed in the cavity 68*a*, e.g., for shipment to a laboratory for processing, or removed from the stand 6 entirely. While embodiments are described in which a sample holder 1 is combined with or used with a stand 6, a stand 6 or other support for a sample holder 1 is not required. Thus, a sample holder 1 can be used for one or more aspects of sample collection, treatment, analysis, etc. with and/or without a stand 6 or other support.

Note that a user of a sample holder can employ the sample holder for one or more different functions. For example, in some cases a user may employ a sample holder only for sample collection. Such a user may collect a sample from the user, e.g., a person may express a blood droplet and use the sample holder to collect the sample, or a person may use a sample holder to collect a sample from another person or other subject. This user may close the sample holder after collection, e.g., by placing a cap on a vessel, and have no further interaction with the sample holder. In some cases, a user may employ a sample holder for treatment and/or analysis of a sample that was previously collected, e.g., by another person. Thus, a user for treatment and/or analysis need not use a sample holder for sample collection and may interact with the sample holder in other ways, such as by opening the vessel, e.g., by removing the upper portion 22 from the lower portion 21 using engagement features on a cap 4, lower portion 21 and/or upper portion 22. Reagents or other materials may be added to the vessel 2, e.g., for processing of the sample in the vessel 2, and/or sample material in the vessel 2 may be removed for treatment and/or analysis, and/or a sample in a vessel may be treated without opening of the vessel 2. Any such users may employ one or more features of a sample holder and/or stand, or not.

The vessel 2 can be made of any suitable material or combination of materials. For example, the lower portion 21 of the vessel can be made of a different material than the upper portion 22 of the vessel 2. Different materials may be employed to help the different vessel portions perform their functions. For example, the lower portion 21 may be made of a material that is suitable for exposing a sample in the holder 1 to focused acoustic energy, heat or other treatment conditions, e.g., for shearing blood cells and/or nucleic acids, PCR amplification, etc. The upper portion 22 can be made of a material that provides a suitable sealing surface with the cap 4 without providing excessive friction that resists movement of the cap 4 relative to the vessel 2. Example materials for the vessel components include polyethylene, polypropylene, glass, metal, etc.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

The invention claimed is:

1. A sample holder comprising:

a vessel having a wall with an outer surface and defining an internal space;

a capillary tube having a distal end positioned in the internal space and a proximal end extending from the internal space through an opening in the wall of the vessel such that the proximal end of the capillary tube is accessible from outside the internal space, the capillary tube configured to receive a blood sample into the proximal end of the capillary tube; and a cap configured to receive the proximal end of the capillary tube and configured to move relative to the vessel such that movement of the cap relative to the vessel from a first position toward a second position causes fluid pressure suitable to move the blood sample from the capillary tube into the internal space and to move fluid from the internal space to an external environment external to the sample holder; and a conduit holder, wherein the capillary tube is supported by the conduit holder, and wherein the conduit holder is distinct from the vessel.

2. The sample holder of claim 1, wherein the cap includes a cavity configured to receive a portion of the vessel to engage the cap with the vessel.

3. The sample holder of claim 2, wherein the cap and the vessel are configured to create a pressure above ambient pressure in response to movement of the portion of the vessel into the cavity.

4. The sample holder of claim 3, wherein the cavity is configured to receive the proximal end of the capillary tube when the cap is engaged with the vessel, and the pressure above ambient pressure is suitable to force the blood sample in the capillary tube to move through the distal end and into the internal space.

5. The sample holder of claim 1, wherein the capillary tube is configured to draw a blood sample into the capillary tube by contacting blood to the proximal end.

6. The sample holder of claim 1, further comprising a desiccant in the internal space configured to dry the blood sample enclosed in the internal space.

7. The sample holder of claim 6, wherein the conduit holder is made of the desiccant and has a tubular shape, and wherein a portion of the capillary tube passes through the desiccant.

8. The sample holder of claim 7, wherein the desiccant engages with an inner surface of the wall of the vessel and supports the capillary tube in the vessel.

9. The sample holder of claim 1, wherein the conduit holder comprises a transparent material that permits a user to see the capillary tube.

10. The sample holder of claim 1, wherein the capillary tube extends through and out of the conduit holder, such that the proximal end of the capillary tube is external to the conduit holder.

11. The sample holder of claim 1, wherein at least a portion of the conduit holder is positioned within the vessel.

12. A method of collecting a blood sample using the sample holder of claim 1, comprising:

providing the capillary tube at least partially within the internal space of the vessel;

contacting blood with the proximal end of the capillary tube to draw the blood into the capillary tube;

moving the cap from the first position toward the second position relative to the vessel to create a positive pressure at the proximal end of the capillary tube and force the blood to move out of the capillary tube and into the internal space of the vessel;

venting fluid from the internal space of the vessel as blood moves into the internal space of the vessel; and positioning the cap at the second position relative to the vessel to seal the internal space closed.

13. The method of claim 12, wherein venting fluid includes venting fluid from the internal space via a fluid pathway defined in part by the opening through the wall of the vessel.

14. The method of claim 13, wherein positioning the cap includes positioning the cap to cover the opening.

15. The method of claim 12, wherein moving the cap includes receiving a portion of the vessel into a cavity of the cap to engage the cap with the vessel and create the positive pressure.

16. The method of claim 12, wherein moving the cap includes moving a volume of gas through the capillary tube from the proximal end to the distal end that is greater than a volume of the capillary tube.

17. The method of claim 12, further comprising drying the blood in the sealed internal space by a desiccant in the internal space.

18. The method of claim 17, wherein providing the capillary tube at least partially within the internal space of the vessel includes using the desiccant to support the capillary tube in the internal space.

19. The method of claim 17, wherein venting fluid includes venting fluid from the internal space via a fluid pathway defined in part by the desiccant.

20. The method of claim 12, wherein moving the cap includes engaging a seal between the vessel and the cap and moving at least a portion of the vessel into the cap to create the positive pressure.

* * * * *